US011992695B2

(12) United States Patent
McCormack et al.

(10) Patent No.: US 11,992,695 B2
(45) Date of Patent: May 28, 2024

(54) APPARATUS FOR TISSUE IRRADIATION AND METHODS AND KITS UTILIZING THE SAME

(71) Applicant: The General Hospital Corporation, Boston, MA (US)

(72) Inventors: Michael C. McCormack, Medford, MA (US); Robert Redmond, Lancaster, MA (US); William G. Austen, Jr., Weston, MA (US); Irene E. Kochevar, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 420 days.

(21) Appl. No.: 16/781,415

(22) Filed: Feb. 4, 2020

(65) Prior Publication Data
US 2021/0001142 A1    Jan. 7, 2021

Related U.S. Application Data

(63) Continuation of application No. 14/849,266, filed on Sep. 9, 2015, now Pat. No. 10,549,112, which is a continuation of application No. PCT/US2014/029896, filed on Mar. 15, 2014.

(60) Provisional application No. 61/788,283, filed on Mar. 15, 2013.

(51) Int. Cl.
*A61N 5/06*    (2006.01)
*A61N 5/00*    (2006.01)

(52) U.S. Cl.
CPC ...... *A61N 5/0601* (2013.01); *A61N 2005/007* (2013.01); *A61N 5/062* (2013.01); *A61N 2005/0656* (2013.01)

(58) Field of Classification Search
CPC .............. A61N 5/0601; A61N 5/062; A61N 2005/007; A61N 2005/0656; A61N 2005/0667; A61N 5/0603; A61B 2018/2261; A61B 2017/00057
See application file for complete search history.

(56) References Cited

U.S. PATENT DOCUMENTS

| 4,612,938 A * | 9/1986 | Dietrich ................. A61B 1/307 606/15 |
| 5,125,925 A * | 6/1992 | Lundahl ............... A61N 5/0601 606/15 |
| 5,709,653 A * | 1/1998 | Leone .................... A61N 5/062 604/20 |

(Continued)

FOREIGN PATENT DOCUMENTS

WO    0007514 A1    2/2000

OTHER PUBLICATIONS

Schmidt et al., Light-Emitting Diodes as a Light Source for Intraoperative Photodynamic Therapy, Neurosurgery, 1996, 38(3):552-557.

*Primary Examiner* — Theodore J Stigell
(74) *Attorney, Agent, or Firm* — Quarles & Brady LLP (57) ABSTRACT

One aspect of the invention provides an apparatus including: a fluid-impermeable membrane configured to contain a fluid and be placed in the cavity; a light emitter provided within the membrane; and a fluid provided within the membrane, wherein the fluid scatters light emitted by the light emitter such that the intensity of the light is substantially uniform over the inner surface of the cavity proximal to the membrane.

15 Claims, 3 Drawing Sheets

(56) References Cited

U.S. PATENT DOCUMENTS

| | | | |
|---|---|---|---|
| 6,251,100 B1 | 6/2001 | Flock et al. | |
| 6,364,874 B1 * | 4/2002 | Bays | A61N 5/0603 |
| | | | 606/15 |
| 7,351,242 B1 * | 4/2008 | Neuberger | A61N 5/062 |
| | | | 606/14 |
| 10,549,112 B2 * | 2/2020 | McCormack | A61N 5/0601 |
| 2002/0087206 A1 * | 7/2002 | Hirschberg | A61N 5/1015 |
| | | | 607/89 |
| 2010/0100160 A1 | 4/2010 | Edman et al. | |
| 2010/0160904 A1 | 6/2010 | McMillan et al. | |
| 2011/0178580 A1 | 7/2011 | Albrecht et al. | |
| 2012/0078160 A1 | 3/2012 | McMillan | |
| 2017/0106013 A1 | 4/2017 | Piergallini et al. | |

* cited by examiner

APPARATUS FOR TISSUE IRRADIATION AND METHODS AND KITS UTILIZING THE SAME

CROSS-REFERENCE TO RELATED APPLICATIONS

This application is a continuation Ser. No. 14/849,266, filed Sep. 9, 2015, which is a continuation of International application No. PCT/US2014/029896, filed Mar. 15, 2014, which published in English as WO 2014/145179 on Sep. 18, 2014, and claims priority to U.S. Provisional patent application Ser. No. 61/788,283, filed Mar. 15, 2013. This application also contains subject matter that may be related to U.S. Provisional patent application Ser. Nos. 61/674,235 and 61/784,708, filed Jul. 20, 2012 and Mar. 14, 2013, respectively, and International application No. PCT/US2013/051333, filed Jul. 19, 2013. The entire disclosures of each of the aforementioned applications are incorporated herein by reference.

BACKGROUND

Application of light or optical energy to a tissue surface can be used in various medical procedures and treatments. For example, light can be applied to a biological tissue surface in order to facilitate healing of a wound site, to remove a stenosis in a blood vessel, for photodynamic therapy (PDT) of tissue, and for photochemical tissue bonding, where light-activated substances can promote adhesion or joining of adjacent tissue surfaces. It has also been observed that application of an appropriate dye to a tissue surface, followed by irradiation with light of an appropriate wavelength, can stabilize the tissue surface and prevent or inhibit scarring and other undesirable healing effects.

In such optical treatments, it may be desirable to apply light energy to an internal tissue surface, e.g., a natural or surgically-formed body cavity or lumen. In a further example, it has been observed that treating a tissue wound surface with an appropriate dye and light (or light alone) intra-surgically can preserve normal tissue architecture, reduce post-surgical inflammation, and reduce or prevent the development of pathogenic collagen bundles (a fibrotic response) following surgery. Such treatment may improve wound healing and lead to reduced adhesion formation, scarring and wound contracture.

Light-based tissue therapy can be used, e.g., to reduce the likelihood or extent of capsular contracture following augmentation mammoplasty with prosthetic implants. Within a decade of surgery, about 50% of patients develop capsular contracture which may lead to significant morbidity and need for reoperation. Currently, there is no preventative treatment available and the recurrence rate remains high, even after capsulectomy.

Neocollagen formation and cross-linking are part of the typical human wound healing response. In capsular contracture, these processes go awry, resulting in dense, linear bundles of collagen fibers that surround the affected implant. These fibers form a firm capsule that subsequently contracts and tightens. Direct pressure from a maturing capsule may deform or rupture the implant, in addition to distorting the overlying skin and soft tissue. The condition may be painful and debilitating as well as aesthetically inferior. Application of light therapy to the interior tissue surface of the implant cavity may reduce or prevent the initial incidence of capsular contracture as well as its recurrence.

Uniformity of light fluence can be important for effective and reliable phototreatment of a tissue surface. However, such uniformity can be difficult to achieve in body cavities or lumens, particularly when they may have an irregular shape. To address this need, various devices have been developed to introduce a light emitter into a body cavity to provide substantially uniform illumination of the surrounding tissue. Such devices typically include a balloon or other flexible membrane that can be introduced into the body cavity, with a light emitter provided within the balloon.

For example, U.S. Pat. No. 5,527,308 of Anderson et al. describes an illuminator device that includes a laser fiber disposed within an optionally expandable optical radiator, wherein the radiator material has particular optical properties (relative diffusivity and reflectivity values) to facilitate uniform irradiation of the surrounding tissue surface. Generally similar illumination devices that can be deployed within a body cavity are described, e.g., in International Patent Publication No. WO 2010/062769 of Gertz et al., and in U.S. Pat. No. 6,364,874 of Bays el al. The uniformity of light fluence on the tissue produced by such devices can be affected by deformation of the membrane or balloon material, which can exhibit nonuniform local variations in thickness when the balloon is expanded or stretched to fill the body cavity or lumen.

Therefore, an illumination apparatus or kit that can provide substantially uniform illumination to the inner surface of a body cavity, which is substantially unaffected by deformation of a membrane or film contacting the inner surface, would be highly desirable.

SUMMARY OF THE DISCLOSURE

Exemplary embodiments of the present disclosure provide an apparatus configured to illuminate a proximal tissue surface with a substantially uniform intensity or fluence of electromagnetic radiation. The apparatus includes a membrane that is impermeable to fluids and is configured to expand to fill, create, or expand a cavity within the biological tissue when filled with a non-gaseous flowable material such as, e.g., a liquid or a gel (herein referred to as a "fluid"). The membrane can be flexible to facilitate introduction into a region of the tissue, and optionally it may be elastic or stretchable. The membrane can be provided in any one of various shapes that can approximately correspond to the shape of the tissue cavity to be irradiated.

The apparatus further includes a light emitter provided within the membrane. The light emitter can include one or more LEDs, or a distal end or region of one or more optical fibers or waveguides. A diffusing object or material such as, e.g., a translucent plastic capsule or the like can be provided around the light-emitting element(s) to improve the local dispersion of the emitted light. An external light generator, such as a laser or LED, can be provided in optical communication with the optical fibers or waveguides, if present. A control arrangement can be provided to control properties of the light generator and/or light emitter such as, e.g., intensity, timing and duration of the emitted light.

The apparatus can also include an access port provided in communication with the interior volume of the membrane, which may be configured to facilitate introduction of fluid into the membrane and/or withdrawal of fluid from the membrane. The access port can further include a valve configured to retain the fluid within the membrane.

The fluid can be selected to scatter light emitted by the light emitter, such that the light intensity or fluence irradiating the interior surface of the membrane and the proximal tissue surface is substantially uniform. In certain embodiments, one or more regions of the membrane can be opaque, reflective, or partially absorptive such that the intensity of light varies over the tissue surface when the light intensity impinging on the interior of the membrane is substantially uniform.

In further embodiments, the apparatus can include a spacing arrangement surrounding at least a portion of the light emitter and configured to maintain a minimum distance between the light emitter and the membrane, e.g., to avoid excessive heating of portions of the membrane and surrounding tissue. In other embodiments, the spacing arrangement can be provided as one or more protrusions or structures affixed to or formed as part of the inner surface of the membrane.

In further embodiments of the disclosure, the light emitter can be a chemiluminescent reaction occurring within at least a portion of the fluid and/or proximal to at least a portion of the membrane.

In yet further embodiments, the apparatus can include a cooling chamber configured to prevent excessive heating or thermal damage of biological tissue adjacent to the membrane. The cooling chamber can be provided proximal to at least a portion of the outer surface of the membrane, or alternatively within the membrane and surrounding at least a portion of the light emitter. The cooling chamber can be provided with an access port to facilitate introduction or withdrawal of a gas or liquid to/from the cooling chamber. Optionally, the cooling chamber can be configured to allow continuous circulation of such gas or liquid therethrough.

In still further exemplary embodiments, the apparatus can include a photoactive substance provided on an outer surface of the membrane, such that the substance is introduced onto or into the tissue surface when the membrane is expanded within the cavity. The substance can be provided in a form that can be released onto or into the tissue by various mechanisms, including but riot limited to a time-release form (e.g. using a dissolvable coating), photoactivated release, pH-activated release, temperature-activated release, etc. Alternatively, the substance can be released into the tissue when a coating or layer provided over the substance and outer membrane surface is mechanically disrupted by expansion of the membrane.

In further exemplary embodiments, the membrane can comprise a tissue expander used in augmentation mammoplasty procedures.

Exemplary embodiments of the present invention can also provide methods for irradiating an interior surface of a biological cavity, which includes the steps of providing a fluid-impermeable membrane into the cavity, introducing a fluid into the membrane to expand it, e.g., such that the membrane contacts the inner surface of the cavity, providing a light emitter within the membrane, and activating the light emitter such that the light emitted therefrom is scattered by the fluid and irradiates the membrane with a substantially uniform intensity or fluence of light.

Another aspect of the invention provides a method of preventing capsular contracture. The method includes introducing an apparatus as described herein into a biological cavity and actuating the apparatus to emit light at a substantially uniform intensity over an inner surface of the cavity proximal to the membrane, thereby preventing capsular contracture.

This aspect of the invention can have a variety of embodiments. The biological cavity can be a surgical incision.

The method can further include applying a photoactive substance to the inner surface of the cavity prior to the introducing step. The photoactive substance can include Rose Bengal.

The light can have a wavelength of about 532 nm.

The method can further include removing the apparatus from the biological cavity and introducing an implantable device into the biological cavity. The implant can be selected from the group consisting of: a breast implant, a pacemaker, an orthopedic prosthesis, a camera, and an optical scanning device.

Another aspect of the invention provides a kit including an apparatus as described herein and a photoactive substance.

This aspect of the invention can have a variety of embodiments. The photoactive substance can include Rose Bengal. The kit can further include instructions for use.

Other features and advantages of the invention will be apparent from the detailed description, and from the claims. Thus, other aspects of the invention are described in the following disclosure and are within the ambit of the invention.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EXEMPLARY EMBODIMENTS

Figure 1:
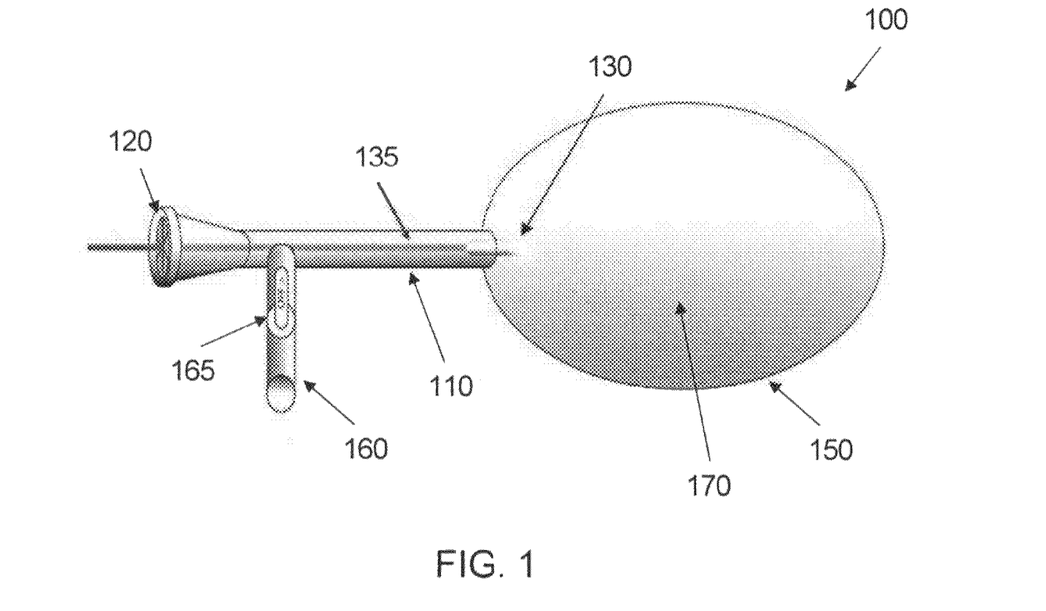
FIG. 1 depicts a first exemplary illumination apparatus in accordance with embodiments of the present disclosure.

An illuminating apparatus 100 in accordance with exemplary embodiments of the present disclosure is shown in FIG. 1. The apparatus 100 can facilitate illumination of a proximal tissue surface with a substantially uniform intensity or fluence of light or other electromagnetic radiation. The apparatus 100 includes a closed membrane 150 configured to contain a fluid, e.g. a balloon or the like, that is coupled to a support body 110. The support body 110 can include a diaphragm or other aperture configured to facilitate introduction of a light emitter 130 into the interior of the membrane 150 using a lead 135 coupled to the light emitter 130, where the lead 135 can extend externally from the support body 110. The support body 110 can further include an access port 160 configured to facilitate introduction and/or removal of a fluid 170 to/from the interior of the membrane 150. The access port 160 can include a valve 165 to retain fluid within the apparatus 100 when a source of fluid is removed from the port 160.

The membrane 150 can be formed of a material that is impermeable to fluids. Optionally, it may be permeable to gaseous species. For example, a gas-permeable membrane 150 can be provided if the apparatus 100 includes a fluid 170 that can support a photochemical reaction that produces nitric oxide, oxygen, singlet oxygen, carbon dioxide, or other gaseous species. The membrane 150 preferably exhibits little or no absorption of light having a desired wavelength passing therethrough (e.g., less than about 5%), for example, having a high transmissivity of the applied light, such as greater than about 95%. Such low absorption/high transmissivity of the membrane material can provide greater efficiency of illumination, such that most of the light emitted by the light emitter 130 irradiates tissue surrounding the membrane 150.

In certain embodiments of the disclosure, optical properties of the membrane 150 can be selected to selectively filter a portion of the light, e.g., to efficiently transmit certain treatment wavelengths of the light produced by the light emitter 130 therethrough, while absorbing or reflecting other wavelengths such that those wavelengths do not irradiate the tissue to a significant degree. The optical properties of the membrane 150 can be determined, e.g., by the membrane material(s), by optically active additives (e.g., reflecting and/or absorbing and/or scattering substances) used to form the membrane 150, and/or by one or more layers of further materials provided on the membrane 150. Optical characteristics of the membrane 150 can be selected based on, e.g., the desired wavelength(s) of light for tissue irradiation and characteristics of the light emitter 130.

In some exemplary embodiments of the disclosure, one or more "shielding" regions of the membrane 150 can be opaque or have a low transmissivity (e.g., less than about 80%) of the wavelength(s) of light used to irradiate the surrounding tissue. Such regions can reduce or eliminate the irradiation from a portion of the interior cavity surface. The change in transmissivity over the surface of the membrane 150 can be discrete (e.g., it can be either substantially transparent or substantially opaque to the light wavelengths), or the transmissivity can vary continuously from high values to lower values in a particular pattern, depending on the desired irradiation pattern for a particular cavity or lumen.

In further embodiments, the membrane 150 can be elastic or stretchable, e.g. like a conventional balloon catheter, such that it can expand to conform to the interior shape of the body cavity when the fluid 170 of an appropriate volume is introduced into the apparatus 100. In still further embodiments, the membrane 150 can be pre-shaped and sized to approximately conform to the body cavity or lumen to be irradiated, with little or no elasticity. Both elastic and relatively inelastic membranes 150 can be provided in a variety of shapes in embodiments of the disclosure, such as spherical or spheroidal, flat or pancake-shaped, hemispherical, cylindrical, etc. The general shape and/or size of the membrane 150 can be selected based on the characteristics of the cavity to be irradiated. The membrane can be sized and/or shaped to be located within anatomical sites including, for example, abdomen, bladder, bowel, chest, colon, intestine, rectum, ovary, uterus, pericardium, peritoneum, mouth, endocardium, or breast The light emitter 130 can be any appropriately-sized light-emitting element that can emit light of sufficient intensity and at one or more desired wavelengths for tissue irradiation. For example, the light emitter 130 can include one or more light-emitting diodes (LEDs), and the associated lead 135 can include electrical wires or the like configured to supply electricity from an external source to the LEDs. Optionally, a power source (e.g., a battery) can be provided on or within the support body 110, optionally with a switch to turn the light emitter 130 on and off. In further exemplary embodiments, a plurality of LEDs can be provided in different orientations, e.g., to generate a broader dispersion of light from the light emitter 130.

The light emitter 130 can also be an emitting region of an optical fiber, a waveguide, or the like. For example, the light emitter 130 can be the distal end or region of an optical fiber, and the lead 135 can include the optical fiber which can be coupled to an external source of light energy (not shown). The external light emitter can be, e.g., a laser, a broadband light emitter, an LED, or any other conventional light-generating arrangement that can provide light of sufficient intensity at the desired wavelength(s) to illuminate tissue surrounding the membrane 150. For example, the external light emitter, if present, can include an argon laser, a tunable dye laser, or the like.

The light emitter 130 can optionally include a diffusing element, e.g., a translucent capsule or the like, which can be provided around the particular light-emitting element(s) to increase the local dispersion of light. In general, the light emitter 130 should be unaffected by the surrounding fluid 170 within the membrane 150. For example, the light emitter 130 can include one or more light-emitting elements that can be surrounded by (or sealed within) a material that is unaffected by contact with the fluid 170. Certain types of light emitters such as, e.g., the distal end of an optical fiber, may be provided directly within the fluid 170.

The support body 110 can be provided in any one of a variety of shapes and sizes. For example, the exemplary shape of the support body 110 shown in FIG. 1 can facilitate insertion and/or withdrawal of the light emitter 130 through the diaphragm 120 and support body 110 using the lead 135. In certain embodiments, the support body 110 can be formed of a rigid material to provide mechanical stability for directing the membrane 150 (and optionally the distal end of the support body 110) into the cavity to be irradiated. In further embodiments, at least a portion of the support body 110 can be flexible, e.g., to allow the support body 110 to better conform to an insertion pathway and/or access structure adjacent to the cavity to be irradiated.

The lead 135 can also be flexible, e.g., it can include one or more optical fibers or waveguides, or electrically conductive wires. In certain embodiments the lead 135 can be rigid, e.g., it can include a stiff sheath, tube, or coating to facilitate more precise placement of the light emitter 130 within the membrane 150. The support body 110 and/or lead 135 can optionally include markings, notches, adjusters (e.g. a threaded coupler) or the like to facilitate more precise and reproducible placement of the light emitter 130 within the membrane 150. In certain embodiments, the support body 110 and/or diaphragm 120 can be frictionally coupled to the lead 135 to facilitate maintenance of a constant position of the light emitter 130 within the membrane 150. The diaphragm 120 can be configured to retain the fluid 170 within the membrane 150 when the light emitter 130 and lead 135 are inserted therethrough. For example, the diaphragm 120 can include one or more O-rings, friction seals, threaded couplers, or the like, which can be selected to form a leak-proof seal with the lead 135 that passes therethrough.

In further embodiments, the apparatus 100 may be provided without a diaphragm 120, with the lead 135 and/or a power source (not shown) for the light emitter 130 provided on or within the support body 110. Such a "self-contained" light arrangement can be configured to provide illumination within the membrane without having the lead 135 protruding from the support body 110.

The access port 160 can be provided in communication with a lumen passing through at least a portion of the support body 110, and configured to direct fluid 170 from an external source into the membrane 150. The access port 160 can be flexible or rigid, and it can be configured to be detachably connected to the outlet of a container, reservoir, supply hose, or the like, e.g., using a conventional fluid hose coupling arrangement or similar connecting element. The valve 165 can be configured to allow fluid flow into or out of the membrane 150 when open, and to retain the fluid 170 within the membrane 150 when it is closed. Any conventional manual or automatic valve arrangement or the like can be used in accordance with embodiments of the disclosure.

In certain embodiments, the valve 165 can include a pressure relief arrangement, which can prevent formation of excessively high fluid pressures within the membrane 150.

The fluid 170 can be introduced into the membrane 150 via the access port 160, such that it may expand the membrane 150 so that the membrane 150 contacts at least a portion of the interior surface of the cavity. The volume of fluid 170 introduced can be selected such that the cavity is just filled by the fluid-filled membrane 150. In certain embodiments, further fluid can be added, e.g., from a pressurized source or reservoir, to expand or enlarge the cavity. In certain embodiments, the membrane 150 can be inserted into a region of tissue, e.g., using a catheter or the like to place it therein, and expanding fluid 170 within the membrane 150 can create a cavity that can then be irradiated.

The fluid 170 can be selected to scatter light emitted from the light emitter 130, which can increase the uniformity of light intensity or fluence over the inner surface of the cavity. For example, the fluid 170 preferably exhibits a very low absorption coefficient (e.g., preferably less than 1%) of light having one or more particular wavelengths that is used to irradiate the cavity walls to achieve a particular biological response. The fluid 170 can also be selected such that it provides significant scattering of the light produced by the light emitter 130, such that the light is spread substantially uniformly through the fluid 170, through the membrane 150, and onto the inner surface of the cavity or lumen being irradiated. In this manner, the apparatus 100 can provide substantially uniform irradiation of the cavity walls without requiring particular optical properties of the membrane material (e.g., reflectivity). The membrane material preferably can have a high transmissivity (e.g., greater than about 90%) for particular wavelengths of light that are provided to irradiate the surrounding tissue, which can improve efficiency of the irradiation process.

The fluid 170 can be a pure liquid, a solution, an emulsion, or a suspension that preferably has low absorption and high degree of scattering or dispersion of the light used to irradiate the cavity walls. For example, the fluid 170 can be a substantially transparent liquid that includes a suspension of small particles, e.g., microscopic or sub-microscopic reflective particles (which may be at least partially metallic) or other types of particles that are small enough to remain suspended in the fluid while exhibiting reflective or scattering properties for the light having irradiation wavelengths of interest.

In further embodiments, the fluid 170 can be a stabilized emulsion of two or more liquids, which can exhibit the desirable scattering properties without being highly absorbing of light. In general, the composition of the fluid 170 (and characteristics of the components thereof such as, e.g., size or concentration) can be selected based on such factors as the intensity and wavelength(s) of light produced by the light emitter 130, the desired irradiation wavelength(s), the size or volume of the cavity to be irradiated, etc. For example, a more highly-scattering fluid may be preferable for membranes that have smaller volumes, whereas a fluid having weaker scattering properties may still provide substantially uniform irradiation over the membrane 150 having a larger volume, and therefore larger distances between the light emitter 130 and the membrane 150.

In still further embodiments, the fluid 170 can be selected such that it absorbs or filters certain wavelengths of light, e.g., if the light emitter 130 is a multi-wavelength or broadband source. In this manner, the fluid 170 can act as a filter to block or reduce the intensity of light of certain wavelengths from reaching the membrane 150 and then irradiating the surrounding tissue of the cavity walls.

A person of ordinary skill in the art can easily test various fluid compositions for a particular light emitter 130 and membrane size and material to achieve the desired transmissivity and scattering properties for substantially uniform dispersion of the light over the membrane surface. In some embodiments of the disclosure, the apparatus 100 can be provided as a kit that includes the device together with a supply of the fluid 170 to be introduced into the membrane 150 as described herein. In certain embodiments, the fluid 170 can include, e.g., an INTRALIPID® fat emulsion available from Fresenius Kabi AB of Uppsala, Sweden, titanium oxide ($TiO_2$) particles, a non-dairy creamer or similar dissolved substance, or the like.

In certain embodiments, the apparatus 100 can be configured to allow it to be retained at least partially within a body for an extended period of time, e.g., several days or weeks. For example, the support body 110 can be configured such that the diaphragm 120 (if present) and/or the proximal end of the access port 160 can be located proximal to an outer surface of the body, when the membrane 150 is located within a cavity or lumen within the body.

Such configuration can facilitate a plurality of irradiation treatments using the light emitter 130 and/or introduction or removal of fluid 170 to the membrane 150 without removing the membrane 150 from the cavity or lumen being treated.

In an exemplary method of irradiating the interior surface of a body cavity or lumen, the membrane 150 of the exemplary apparatus 100 can be introduced into the cavity, e.g., in a collapsed state. The apparatus 100 can be introduced via a naturally-occurring passage in the body or by a cut or surgically-created opening. The apparatus 100 can be positioned such that the access port 160 and/or the diaphragm 120 (if present) can be accessed from outside the body.

Fluid 170 can then be introduced into the membrane 150 via the access port 160 to expand the membrane 150, such that it substantially fills the cavity to be irradiated. For example, the membrane 150 can be expanded such that it contacts substantially all of the interior surface of the cavity. The membrane 150 can be filled with a particular volume of the fluid 170, e.g., approximately corresponding to the original or desired volume of the cavity. The source of the fluid 170 can optionally be detached from the access port 160 after the membrane 150 is filled and the valve 165 closed to seal the fluid 170 within the apparatus 100.

The light emitter 130 can then be activated for a particular duration to irradiate the interior of the cavity. A control arrangement (not shown) can optionally be provided to control the duration, timing, intensity and/or other parameters of the light provided by the light emitter 130. The light emitter 130 can be withdrawn from the apparatus 100 after irradiation, and reinserted later for subsequent irradiation. Alternatively, the light emitter 130 can remain within the apparatus 100 between irradiation procedures.

Figure 2:
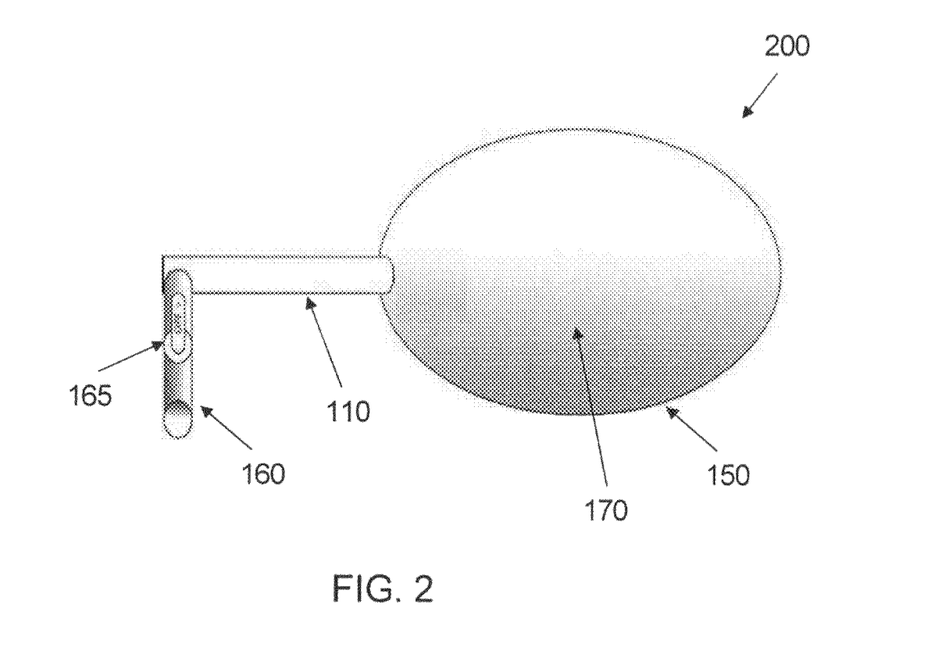
FIG. 2 depicts a second exemplary illumination apparatus in accordance with further embodiments of the present disclosure.

A second illumination apparatus 200 in accordance with further exemplary embodiments of the present disclosure is shown in FIG. 2. The apparatus 200 can include a membrane 200, support body 110, access port 160 and valve 165, similar to those described above with respect to apparatus 100 shown in FIG. 1. The apparatus 200 can be deployed in a body cavity to be irradiated as described above with respect to apparatus 100.

The apparatus 200 may be provided with a fluid 170 within the membrane that is chemiluminescent or includes one or more substances capable of undergoing or activating a chemiluminescent reaction. Such a chemiluminescent reaction in the fluid 170 can generate light that illuminates the cavity walls proximal to the membrane 150. The fluid 170 can be introduced to the interior of the membrane 150 via the access port 160. In certain exemplary embodiments, a first component of the chemiluminescent reaction can be provided within the membrane, such that the reaction is activated when the fluid 170 is introduced into the membrane 170 and contacts or mixes with the first component. For example, the first component can mix uniformly with the fluid 170 to generate light substantially uniformly throughout the volume of fluid 170. In further embodiments, the first component can be provided on at least a portion of the inner surface of the membrane 150, such that the chemiluminescent reaction occurs primarily in a region close to the membrane and surrounding cavity walls. In still further embodiments, the chemiluminescent reaction can be initiated in the fluid 170 prior to introducing it into the apparatus 200. The membrane 150 can be shaped, e.g., to include one or more regions configured to enter small cavities and provide illumination therein. Uniform illumination of such small cavities may be difficult to achieve using conventional devices such as fiber optic probes.

Various known chemical systems capable of generating light via a chemical reaction can be used with the apparatus 200. The particular chemiluminescent system can be selected based on such factors as, e.g., the wavelength(s) of light and areal or volumetric intensity of light emitted by the reaction, the volume or size of the cavity to be irradiated, etc. In some embodiments of the disclosure, the apparatus 200 can be provided as a kit that includes the device together with a supply of the chemiluminescent fluid 170 to be introduced into the membrane 150 as described herein. For example, chemiluminescent materials or systems that can be used with embodiments of the present disclosure include, but are not limited to, luciferin/luciferase, horseradish peroxidase systems, luminol, or the like.

In further embodiments of the disclosure, a photoactive substance or precursor of a photoactive substance, such as ALA that can be used in photodynamic therapy (PDT) procedures, can be provided on an outer surface of the membrane 150 in the apparatus 100, 200. This substance can be transferred onto the tissue surface of the cavity wall when the membrane 150 is expanded within the cavity, as described herein, and subsequently activated with light energy as described herein. An apparatus configured to apply a photoactive substance from an expandable balloon onto a surrounding tissue surface is described, e.g., in European Patent No. EP 1039944 of Leone et al. For example, the photoactive material or precursor can be introduced to the tissue surface by contact adsorption. Any photoactive substance or precursor of a photoactive substance that can be used in conventional phototherapy procedures may be used with embodiments of the present disclosure.

In further embodiments, the photoactive material can be released from the membrane 150 onto the surrounding tissue by various mechanisms. For example, the photoactive substance or precursor can be released by a light-initiated reaction (photoactivation), where the light used to release the substance can be generated by the light emitter 130 and may be the same as or different than the light used to irradiate the tissue itself (e.g., the releasing light may have a different wavelength and/or different intensity or fluence than the treatment light). In further embodiments, the substance can be released by a time-release reaction, e.g., through dissolution of a protective coating activated by contact with the tissue itself (which can occur by simple liquid-based dissolution), by a change in local pH when the membrane is contacting the tissue cavity walls, by a change in temperature (e.g. by warming to body temperature), etc. In a still further embodiment, the photoactive material provided on the outer surface of the membrane 150 can be coated by a flexible but non-expandable layer of material. The integrity of this coating can be broken when the membrane 150 is expanded, thereby exposing the underlying photoactive material to the surrounding tissue surfaces.

Figure 3:
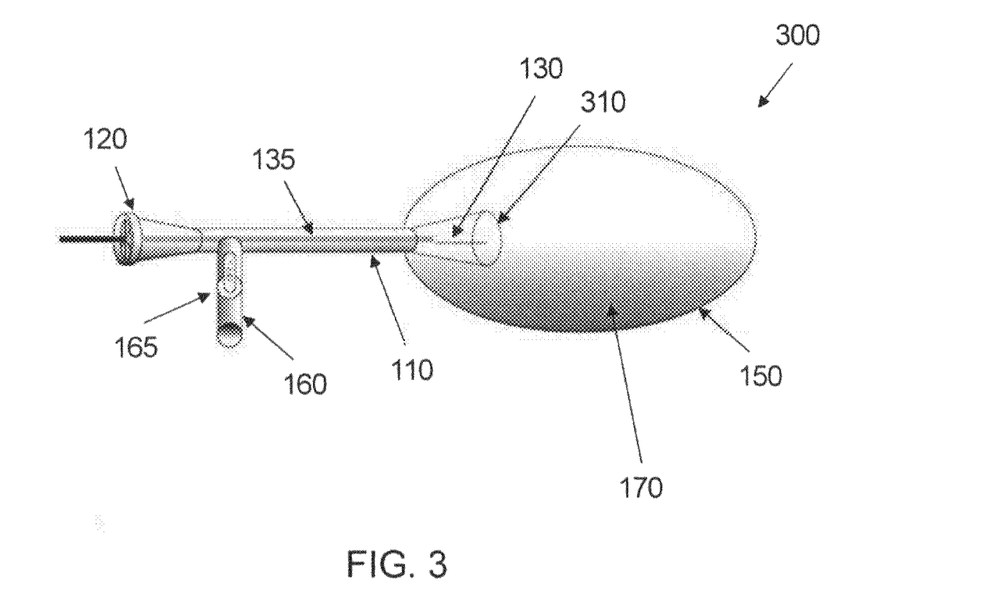
FIG. 3 depicts a third exemplary illumination apparatus in accordance with embodiments of the present disclosure.

The light emitter 130 can also be a local source of heat. Such heat may not be desirable in certain uses, e.g., the light emitter 130 could be located close to a portion of the membrane 150 and cause unwanted heating of adjacent tissue. FIG. 3 illustrates an exemplary apparatus 300 in accordance with further embodiments of the disclosure. The apparatus 300 can be similar to the apparatus 100 shown in FIG. 1 and described herein, and further includes a spacing arrangement 310 provided proximal to the light emitter 130. The spacing arrangement 310 can help to maintain a particular minimum distance or spacing between the light emitter 130 and the inside walls of the membrane 150, which can avoid excessive heating of the membrane 150 and adjacent tissue. Maintaining at least a particular distance between the light emitter 130 and the inside walls of the membrane 150 can also prevent or reduce the likelihood of having a higher fluence along one portion of the membrane 150, e.g., by ensuring that light from the light emitter 130 must travel through at least the particular distance through the scattering fluid 170, which can provide a more uniform light fluence or intensity at the membrane 150. The spacing arrangement 310 can prevent contact between the light emitter 130 and the inside walls of the membrane 150 when the membrane 150 is deformed or deflated/collapsed within the body cavity or lumen surrounding the membrane 150. The spacing arrangement 310 can be provided with any of the various embodiments described and illustrated herein.

In certain embodiments, the spacing arrangement 310 can be formed of a material that is substantially transparent optically. Alternatively, the spacing arrangement 310 can be formed of a material that can scatter or diffuse light, e.g., to provide a more spatially uniform dispersion of emitted light into the surrounding fluid 170. The spacing arrangement 310 can be rigid, or it can be provided as a collapsible or compressible structure that can expand when the light emitter 130 is inserted or positioned within the membrane 150. The spacing arrangement 310 can be provided in various shapes that may differ from the particular embodiment shown in FIG. 3.

In further embodiments (not illustrated), the spacing arrangement 310 can be provided as one or more protrusions or structures affixed to or formed as part of the inner surface of the membrane 150. Such protrusions or structures can contact the light emitter 130 and/or the lead 135 coupled thereto to prevent the light emitter 130 from contacting or approaching the inner surface of the membrane 150.

Figure 4:
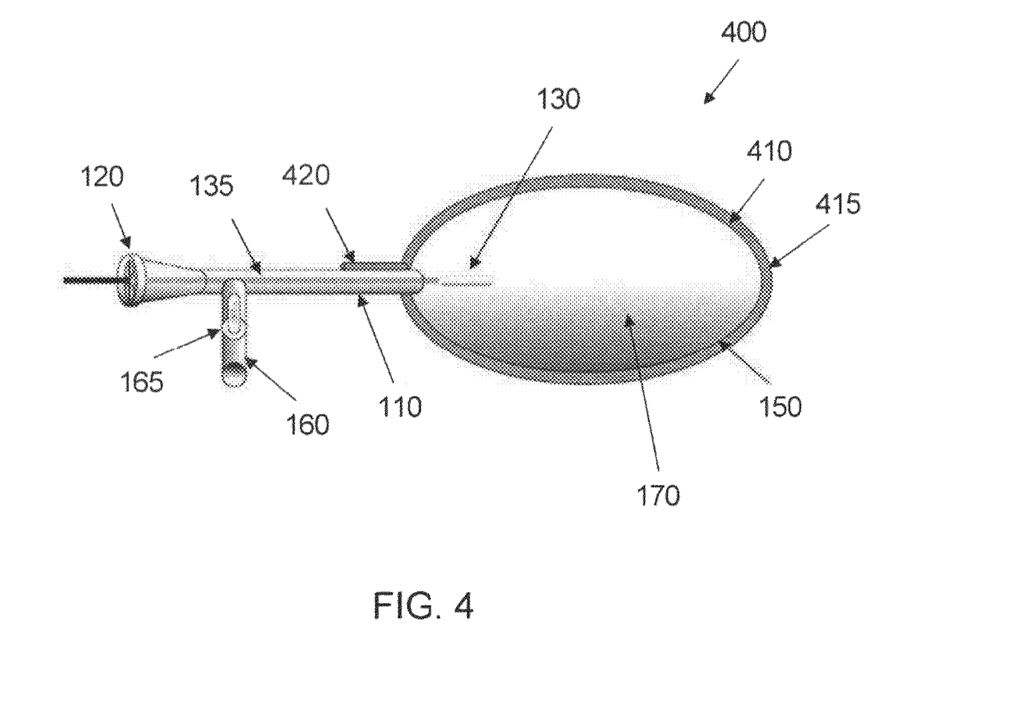
FIG. 4 depicts a fourth exemplary illumination apparatus in accordance with embodiments of the present disclosure.

An apparatus 400 in accordance with still further exemplary embodiments of the disclosure is shown in FIG. 4. The apparatus 400 can be similar to the apparatus 100 shown in FIG. 1 and described herein, and further includes a cooling chamber 410. The cooling chamber 410 can facilitate cooling of the tissue cavity or lumen surrounding the apparatus 400, e.g., during, prior to and/or after irradiation of the tissue with light provided by emitter 130. As shown in FIG. 4, cooling chamber 410 can be provided proximal to the membrane 150, e.g., in the form of a chamber 410 located between the outer surface of the membrane 150 and a chamber surface 415 surrounding at least a portion of the membrane 150.

The chamber surface 415 can be formed of a flexible or elastic material, e.g., similar to the material used to form the membrane 150. The chamber surface 415 can be affixed to one or more portions of the outer surface of the membrane 150, for example, to provide or maintain a particular thickness or volume, or shape of the cooling chamber 410 around the membrane 150. Optionally, the chamber surface 415 can be affixed to one or more portions of the outer surface of the membrane 150 to form one or more channels within the cooling chamber 410, e.g., to facilitate flow of liquid or gas therethrough.

The cooling chamber 410 can be filled with an insulating substance such as air or another gas, or a cooling fluid can be provided therein. Access to the interior volume of the cooling chamber 410 can be provided, e.g., by an access tube 420 or the like. Such access tube 415 can be used to introduce and/or withdraw a gas or fluid from the cooling chamber 410. In certain embodiments, the cooling chamber 410 can be provided with two or more access tubes 420, e.g., to facilitate periodic or continuous introduction of and withdrawal of gas or liquid, e.g., to circulate such gas or liquid through the cooling chamber 410. The proximal end of the access tube 415 can be provided in various locations, and can be configured to facilitate access thereto when the membrane 150 is placed in a body cavity or lumen. In certain embodiments, a portion of the access tube 420 can be located adjacent to or within the support body 110.

In further exemplary embodiments, the cooling chamber 410 can be provided within the membrane 150, e.g., adjacent to and at least partially surrounding the light emitter 130. For example, the cooling chamber 410 can have the shape of a capsule or the like surrounding the light emitter 130, which can reduce heating of the scattering fluid 170 within the membrane 150. The cooling chamber 130 in such a configuration (not illustrated) can also provide benefits and functions similar to that of the spacing arrangement 310 shown in FIG. 3 and described herein. A cooling chamber 410 as described herein can be used with any embodiments of the present disclosure, including the apparatus 100, 200, 300 shown in FIGS. 1-3.

In one example, the apparatus 100, 200, 300, 400 can be used to treat a tissue surface with an appropriate photoactive agent and light, intra-surgically, to reduce post-surgical inflammation and/or prevent the development of pathogenic collagen bundles (i.e., fibrotic response) following surgery.

For example, the method and apparatus described herein can be used to reduce or eliminate the occurrence of capsular contraction in an augmentation mammoplasty procedure with prosthetic implants. In this exemplary procedure, the membrane 150 can be a shaped tissue expander commonly used in such procedures. The apparatus can be used to activate a photoactive substance such as, e.g., a 0.1% Rose Bengal solution, that can be applied to the inside surfaces of an implant cavity and then irradiated with light at about 532 nm wavelength. The light can be provided to the interior of the membrane 150, e.g., by a continuous wave frequency double Nd/YAG laser using an optical fiber arrangement. The membrane 150 can be left in the chest cavity during formation and expansion of the cavity, e.g., for about 1-4 weeks. Fluid 170 can be added periodically via the access port 160 to further expand and stretch the cavity over time. The exemplary apparatus 100, 200 can be used to re-irradiate the interior of the cavity after such fluid additions. The dye can be re-applied or provided in a timed-release form such that it is present on the expanded cavity surfaces prior to each irradiation using the apparatus 100, 200. This exemplary procedure can be used to "passivate" the tissue surfaces within the cavity, thereby reducing or eliminating undesirable capsular contraction.

Figure 5:
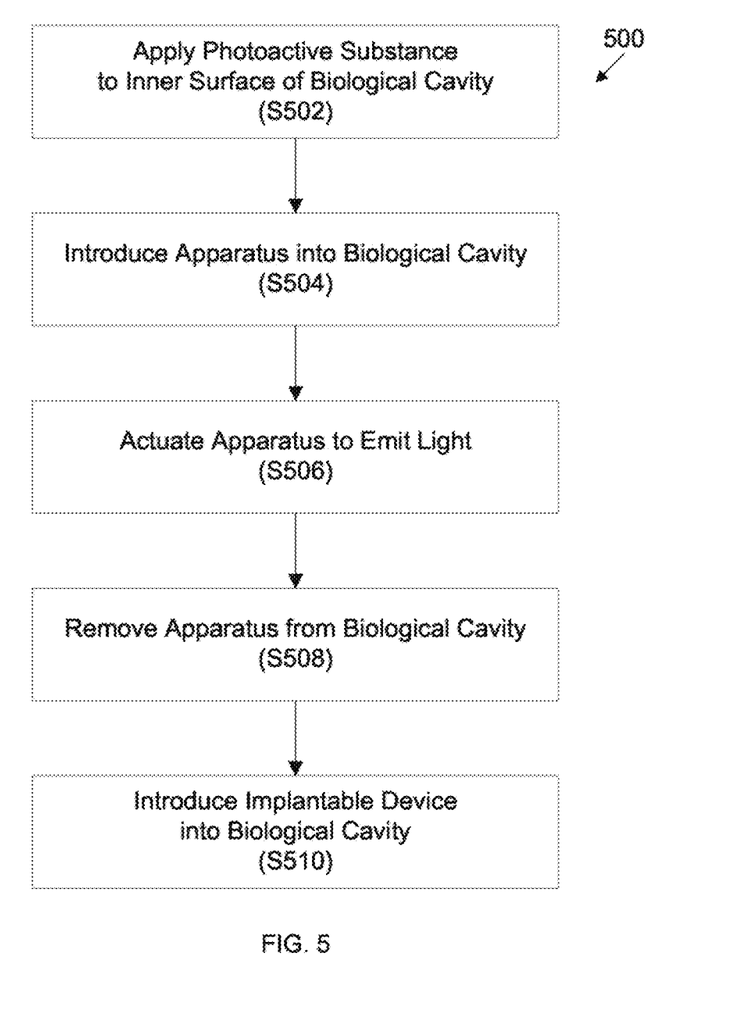
FIG. 5 depicts a method of preventing capsular contracture in accordance with embodiments of the present disclosure.

Referring now to FIG. 5, a method 500 of preventing capsular contracture is provided. Method 500 can be performed on any living subject, especially a mammal such as a human.

In step S502, a photoactive substance is optionally applied to an inner surface of a biological cavity. Photoactive substances typically have chemical structures that include multiple conjugated rings that allow for light absorption and photoactivation. A number of photoactive agents are known to one of skill in the art, and generally include a variety of light-sensitive dyes and biological molecules. Examples include, but are not limited to: xanthenes, e.g., Rose Bengal ("RB") and erythrosin; flavins, e.g., riboflavin; thiazines, e.g., methylene blue (MB); porphyrins and expanded porphyrins, e.g., protoporphyrin I through protoporphyrin IX, coproporphyria, uroporphyrins, mesoporphyrins, hematoporphyrins and sapphyrins; chlorophylls, e.g., bacteriochlorophyll A, phenothiazine (e.g., Toluidine Blue), cyanine, Mono azo dye (e.g., Methyl Red), Azine mono azo dye (e.g., Janus Green B), rhodamine dye (e.g., Rhodamine B base), benzophenoxazine dye (e.g., Nile Blue A, Nile Red), oxazine (e.g., Celestine Blue), anthroquinone dye (e.g., Remazol Brilliant Blue R), riboflavin-5-phosphate (R-S-P) and N-hydroxypyridine-2-(I H)-thione (N-HTP) and photoactive derivatives thereof.

The biological cavity can be formed by a surgical incision and can be a pocket or other region designed to receive an implantable device.

The photoactive substance can be applied to the inner surface by a number of tools and techniques including a brush, syringe, cannula, sprayer, atomizer, and the like.

In step S504, an apparatus 100, 200, 300, 400 as described herein is introduced into the biological cavity. The apparatus 100, 200, 300, 400 can be initially deflated for insertion through an incision and later inflated once positioned within the cavity so as to press against an inner surface of the cavity.

In step S506, the apparatus 100, 200, 300, 400 is actuated to emit light. The intensity, frequency, wavelength, and/or duration of the emitted light can be selected to activate the photoactive compound. For example, light having a wavelength of about 542 nm can be utilized to activate Rose Bengal.

In step S508, the apparatus 100, 200, 300, 400 is removed from the cavity. In some embodiments, this can be accomplished by deflating the apparatus in order to pass through an incision.

In step S510, an implantable device is inserted into the biological cavity. Examples of implantable devices include a breast implant, a pacemaker, an orthopedic prosthesis, camera, optical device, and the like.

Figure 6:
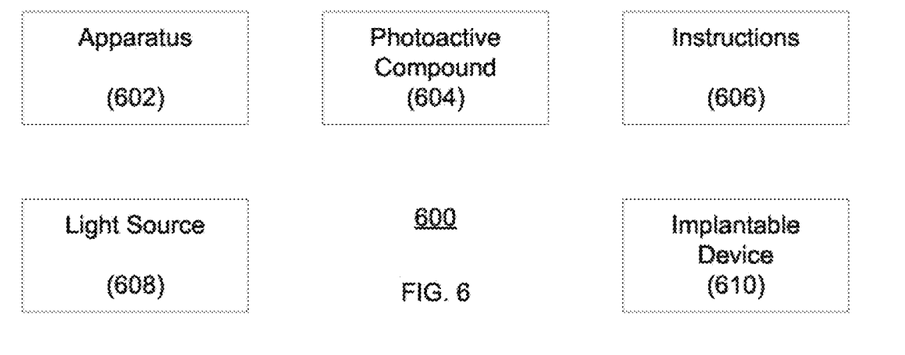
FIG. 6 depicts a kit in accordance with embodiments of the present disclosure.

Referring now to FIG. 6, a kit 600 is provided. Kit 600 can include one or more of an apparatus 602 as described herein, a photoactive compound 604, instructions for use of the apparatus 602 (e.g., according to method 500), a light source 608 (e.g., a light source capable of providing light to apparatus 602), and an implantable device 610 (e.g., a breast implant, a pacemaker, an orthopedic prosthesis, camera, optical device, and the like).

Although the present disclosure has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the present disclosure and should not be construed to limit the scope thereof.

It will thus be appreciated that those skilled in the art will be able to devise numerous systems, arrangements and methods which, although not explicitly shown or described herein, embody the principles of the present disclosure and are thus within the spirit and scope of the present disclosure.

The invention claimed is:

1. An apparatus for irradiating the inner surface of a biological cavity, comprising:
   a fluid-impermeable membrane configured to contain a fluid and be placed in the cavity;
   a light emitter extending into the fluid-impermeable membrane from a support that is proximal and external to the fluid-impermeable membrane;
   a fluid provided within the fluid-impermeable membrane from the support, wherein the fluid scatters light emitted by the light emitter such that the intensity of the light is substantially uniform over the inner surface of the cavity proximal to the fluid-impermeable membrane; and
   a spacing arrangement provided proximal to the light emitter such that the spacing arrangement does not extend distally past the light emitter and within the fluid-impermeable membrane, wherein the spacing arrangement is configured to maintain a minimum distance between the light emitter and an inside wall of the fluid-impermeable membrane.

2. The apparatus of claim 1, further comprising an access port coupled to the interior volume of the fluid-impermeable membrane, wherein the access port is configured to facilitate at least one of introduction of the fluid into the fluid-impermeable membrane or removal of the fluid from the membrane.

3. The apparatus of claim 1, further comprising a valve coupled to an access port.

4. The apparatus of claim 1, further comprising a pressure relief arrangement.

5. The apparatus of claim 1, wherein the fluid-impermeable membrane is formed of an elastic material.

6. The apparatus of claim 1, wherein the fluid is at least one of a solution, a suspension, or an emulsion.

7. The apparatus of claim 1, further comprising a diaphragm coupled to the interior volume of the fluid-impermeable membrane, wherein the diaphragm is configured to facilitate introduction of the light emitter into the interior volume of the fluid-impermeable membrane.

8. The apparatus of claim 1, wherein the light emitter comprises at least one of an LED or a distal region of an optical fiber.

9. The apparatus of claim 1, further comprising at least one of a photoactive substance or a precursor to a photoactive substance that is provided on an outer surface of the fluid-impermeable membrane.

10. The apparatus of claim 9, wherein the photoactive substance or precursor is provided in a form that can be controllably released onto the inner surface of the cavity when the fluid-impermeable membrane is placed in the cavity.

11. The apparatus of claim 1, further comprising a cooling chamber.

12. The apparatus of claim 1, wherein the light emitter comprises one or more substances capable of at least one of undergoing or activating a chemiluminescent reaction within at least a portion of the fluid.

13. The apparatus of claim 1, wherein the light emitter comprises one or more substances capable of at least one of undergoing or activating a chemiluminescent reaction on at least a portion of the fluid-impermeable membrane.

14. The apparatus of claim 1, wherein the spacing arrangement is formed of a material that can scatter or diffuse light.

15. An apparatus for irradiating the inner surface of a biological cavity, comprising:
   a fluid-impermeable membrane configured to contain a fluid and be placed in the cavity;
   a light emitter extending into the fluid-impermeable membrane from a support that is proximal and external to the fluid-impermeable membrane;
   a fluid provided within the fluid-impermeable membrane from the support, wherein the fluid scatters light emitted by the light emitter such that the intensity of the light is substantially uniform over the inner surface of the cavity proximal to the fluid-impermeable membrane; and
   a spacing arrangement provided proximal to the light emitter and within the fluid-impermeable membrane, wherein the spacing arrangement is spaced away from the light emitter so as to maintain a minimum distance between the light emitter and an inside wall of the fluid-impermeable membrane.

* * * * *

UNITED STATES PATENT AND TRADEMARK OFFICE
CERTIFICATE OF CORRECTION

PATENT NO. : 11,992,695 B2
APPLICATION NO. : 16/781415
DATED : May 28, 2024
INVENTOR(S) : Michael C. McCormack et al.

It is certified that error appears in the above-identified patent and that said Letters Patent is hereby corrected as shown below:

In the Claims

Claim 2, Column 13, Line 60, "membrane" should be --fluid-impermeable membrane--.

Signed and Sealed this
Twelfth Day of November, 2024

Katherine Kelly Vidal
*Director of the United States Patent and Trademark Office*